United States Patent [19]

Verboven-Nelissen

[11] Patent Number: 5,720,768

[45] Date of Patent: Feb. 24, 1998

[54] DUAL CHAMBER PACING WITH INTERCHAMBER DELAY

[75] Inventor: Yves Verboven-Nelissen, Kessel-LO, Belgium

[73] Assignee: Sulzer Intermedics Inc., Angleton, Tex.

[21] Appl. No.: 651,741

[22] Filed: May 22, 1996

[51] Int. Cl.[6] ................................................. A61N 1/368
[52] U.S. Cl. ................................................................ 607/9
[58] Field of Search ........................ 607/9, 14; 128/697

[56] References Cited

U.S. PATENT DOCUMENTS

| | | |
|---|---|---|
| 3,937,226 | 2/1976 | Funke . |
| 4,088,140 | 5/1978 | Rockland et al. . |
| 4,354,497 | 10/1982 | Kahn . |
| 4,549,548 | 10/1985 | Wittkampf et al. ...................... 607/27 |
| 4,817,605 | 4/1989 | Sholder . |
| 4,858,610 | 8/1989 | Callaghan et al. ...................... 607/13 |
| 5,027,815 | 7/1991 | Funke et al. . |
| 5,165,403 | 11/1992 | Mehra . |
| 5,273,035 | 12/1993 | Markowitz et al. ...................... 607/14 |
| 5,282,837 | 2/1994 | Adams et al. ...................... 607/5 |
| 5,314,430 | 5/1994 | Bardy ...................... 607/5 |
| 5,403,356 | 4/1995 | Hill et al. . |
| 5,423,772 | 6/1995 | Lurie et al. ...................... 604/282 |
| 5,514,161 | 5/1996 | Limousin ...................... 607/9 |
| 5,571,143 | 11/1996 | Hoegnelid et al. ...................... 607/9 |
| 5,584,867 | 12/1996 | Limousin et al. ...................... 607/9 |

OTHER PUBLICATIONS

M. Akhtar, et al. "Mechanism of Clinical Tachycardias," *American Journal of Cardiology*, (1988), vol. 61, pp. 9A–19A.

S. Barold, "Modern Cardiac Pacing," (1985), pp. 214–279.

S. Cazeau, et al., "Four Chamber Pacing in Dilated Cardiomyopathy," *Pace*, (Nov. 1994), vol. 17, pp. 1974–1975.

M. Rosen, "Mechanisms for Arrhythmias," *American Journal of Cardiology*, (1988), vol. 61, pp. 2A–8A.

M. Rosenqvist, et al., "Long-term Pacing in Sinus Node Disease: Effects of Stimulation Mode on Cardiovascular Morbidity and Mortality," *American Heart Journal*, (Jul. 1988), vol. 116, No. 1, Part 1, pp. 16–22.

G. Klein, et al., "Demonstration of Macroreentry and Feasibility of Operative Therapy in the Common Type of Atrial Flutter," *Journal of Cardiology*, (1986), vol. 57, pp. 587–591.

G. Lamas, et al., "Does Dual Chamber or Atrial Pacing Prevent Atrial Fibrillation? The Need for a Randomized Controlled Trial," *Pace*, (Aug. 1992), vol. 15, pp. 1109–1113.

J. Fischer, "Electrical Devices for Treatment of Arrhythmias", *American Journal of Cardiology*, (1988), vol. 61, pp. 45A–57A.

M. Hewitt, "Coronary Sinus Atrial Pacing: Radiographic Considerations," *AJR*, (Feb. 1981), vol. 136, pp. 323–328.

C. Kerr, et al., "Atrial Fibrillation: Fact, Controversy & Future" vol. 3, No. 5, pp. 319–337. (1985).

F. Cosio, et al., "Validation of Double–Spike Electrograms as Markers of Conduction Delay or Block in Atrial Flutter," *American Journal of Cardiology*, (1988), vol. 61, pp. 775–780.

J. Daubert, "Synchronous Biatrial Stimulation: Recent Technological Progress," *Stimucoeur*, (May 1995), vol. 23, No. 2, pp. 156–158.

*Primary Examiner*—Jeffrey R. Jastrzab
*Attorney, Agent, or Firm*—John R. Merkling

[57] ABSTRACT

A method and apparatus for determining the origin of a cardiac signal in the heart of a patient. A cardiac stimulator includes a multiple-chamber electrode arrangement having at least two electrodes positioned to sense and/or pace different chambers of the heart. The electrodes switch from a bipolar configuration to a unipolar configuration in order to verify the point of origin for the cardiac signal and in order to determine whether propagation of the cardiac signal occurs. The apparatus allows simultaneous and timed pacing of left and right chambers.

16 Claims, 6 Drawing Sheets

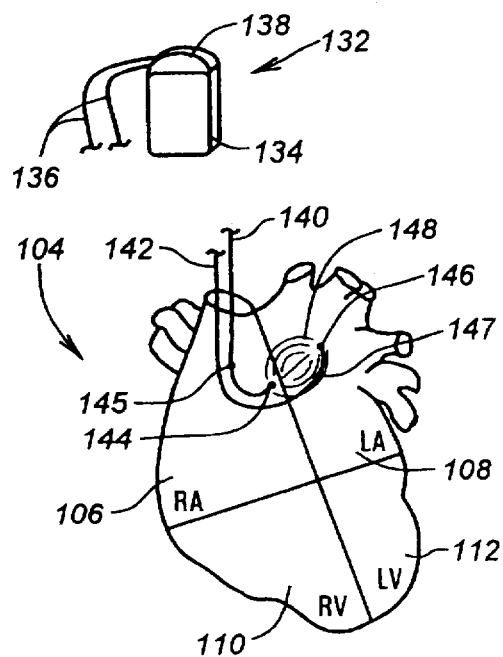
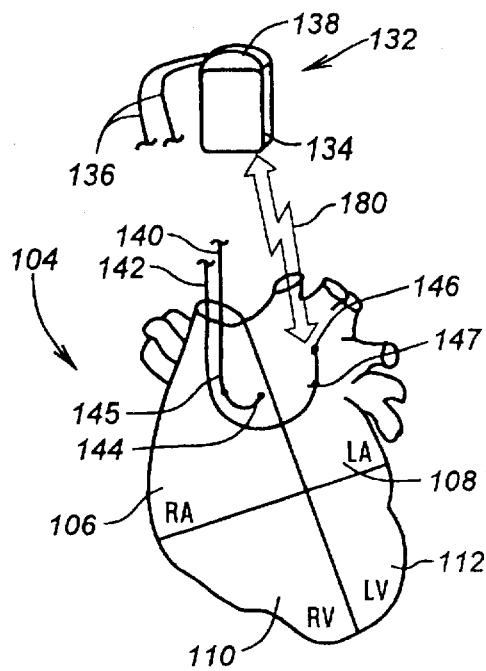
FIG. 4A                FIG. 4B
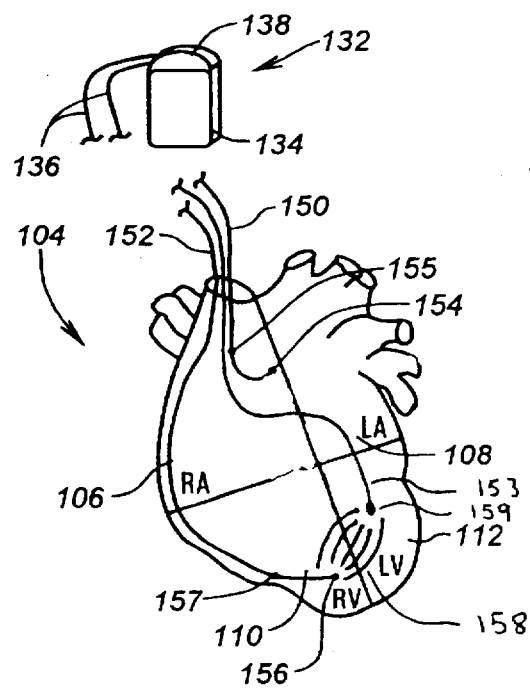
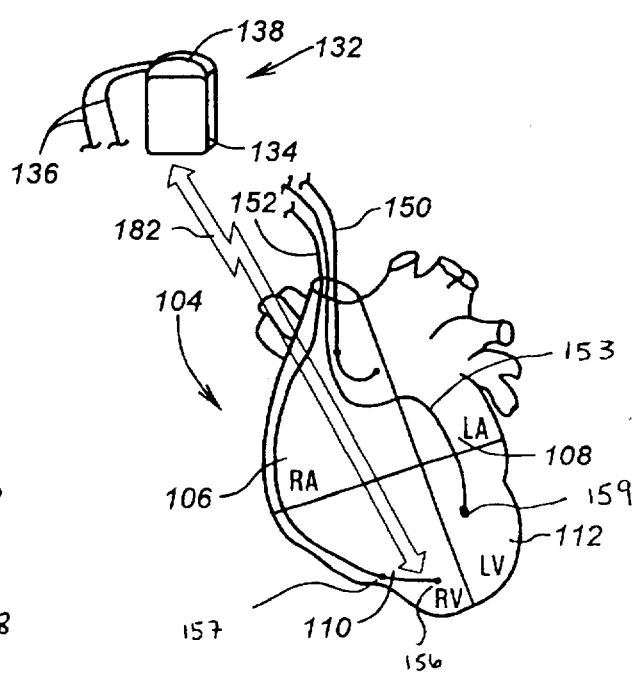
FIG. 5A                FIG. 5B

DUAL CHAMBER PACING WITH INTERCHAMBER DELAY

BACKGROUND OF THE INVENTION

Pacemakers, defibrillators, and pulse generators may employ various multiple-chamber electrode arrangements in the hearts of patients. Four chamber pacing, for instance, can be used in patients having obstructed cardiomyopathy, DDD syndrome, dilated cardiomyopathy, extended intra-atrial or intra-ventricular conduction times, left originated flutters, or atrial fibrillations. In obstructed or dilated cardiomyopathy, one or two electrodes are positioned in the left and/or right atrium and one electrode in the left and/or right ventricle. In this multiple-chamber arrangement, when the electrode in the atrium detects a cardiac signal, the atrial electrodes may stimulate the atria and one or both of the ventricular electrodes may stimulate the ventricles. The multiple-chamber electrodes thus work in conjunction to pace and sense all four chambers of the heart.

Other multiple-chamber electrode arrangements are employed in patients as well. Dual chamber pacing, for example, may be used to prevent, detect and/or treat atrial fibrillation. In one possible arrangement, a unipolar lead is positioned in the right atrium, and a bipolar lead is positioned, via the coronary sinus, adjacent to the left atrium. When a bipolar detection between both leads is made, a verification of the origin can be made and if a left sided origin exists, the right atrial lead can immediately stimulate the right atrium. This stimulation causes the right atrium to depolarize and thus halt propagation of the ectopic signal.

As one disadvantage, prior multiple-chamber electrode arrangements do not determine the origination of a cardiac signal, especially when such signals originate as ectopic or extraneous beats. A dual chamber pacing system treating atrial arrhythmias, for example, may not be able to distinguish between an ectopic flutter originating in the left atrium and a normal conduction signal originating at the SA node. In one study, for example, clinicians used a DDD pacemaker with patients experiencing chronic atrial fibrillation. The clinicians evaluated the problem of the pacemaker inappropriately sensing spontaneous atrial fibrillations and stated:

> Since currently available devices sense primarily amplitude, there is no reliable way for DDD pacemakers to discriminate atrial fibrillation from sinus rhythm. Therefore, there is potential for tracking of atrial fibrillation to the upper rate limit of the pacemaker.

C. R. Kerr, et. al, "Atrial Fibrillation: Fact, Controversy, and Future," *Clin. Prog. Electrophysiol. and Pacing*, Vol. 3, No. 5 (1985), pp. 329–330.

As another disadvantage, prior multiple-chamber electrode arrangements do not track or verify propagation of the cardiac conduction signal and thus may stimulate even during periods of normal conduction. Some dual chamber pacing systems employ two atrial leads to detect and treat atrial arrhythmia. Pacing, however, may occur in both atria even though the cardiac conduction signal originated at the SA node and would have properly propagated to the left atrium. As such, the atrial leads do not verify whether the cardiac signal properly propagates to the left atrium—in spite of possible normal propagation from the SA node.

It therefore would be advantageous to provide a multiple-chamber electrode arrangement that verifies the origination of a cardiac signal propagating in the heart of the patient. Such a system would be able to recognize and then distinguish between abnormal signals originating in the ventricles or atria and normal cardiac conduction signals originating at the SA node.

Additionally, it would be advantageous to provide a multiple-chamber electrode arrangement which recognizes a normal cardiac conduction signal originating at the SA node and then verifies whether this signal properly propagates to other chambers in the heart. Such a system would not stimulate unnecessarily during proper cardiac conduction. Further, battery longevity of the pacemaker or pulse generator would be enhanced.

SUMMARY OF THE INVENTION

The present invention is addressed to a method and an apparatus for determining the originating location of a cardiac signal in the heart of a patient. In addition, once a cardiac signal is detected and its location verified, the present invention confirms depolarization and propagation of the cardiac signal from one chamber of the heart to another adjacent chamber.

The apparatus of the present invention includes a multiple-chamber electrode arrangement having at least two electrodes placed to sense and/or pace different chambers or areas of the heart. The electrodes initially are in a bipolar configuration for sensing cardiac signals originating in the heart. Once a cardiac signal is sensed, the electrodes are immediately switched to a unipolar configuration. In order to verify the point of origin for the cardiac signal, the electrodes then re-sense for the presence of the signal in different chambers of the heart where the electrodes may be located. The immediate detection or non-detection of the cardiac signal at an electrode confirms the originating location of the signal.

Additionally, the present invention confirms whether a normal cardiac conduction signal originating at the SA node or initiated after a pace in the right atrium propagates from the right atrium to other chambers within the heart. In this regard, once a cardiac signal originates at the SA node, the present invention senses this signal in the right atrium and then commences timing of a conduction interval. This conduction interval represents the time required for the cardiac signal to properly depolarize from the right atrium to another chamber of the heart. If the conduction interval elapses and the cardiac signal did not propagate to the appropriate chamber, then a therapy is initiated. If, on the other hand, proper propagation occurs, no therapy is initiated.

The invention, accordingly, comprises the apparatus and method possessing the construction, combination of elements, and arrangement of parts which are exemplified in the following detailed description. For a fuller understanding of the nature and objects of the invention, reference should be made to the following detailed description taken in connection with the accompanying drawings.

BRIEF DESCRIPTION OF THE DRAWINGS

FIG. 4A is a schematic representation of a heart employing a bipolar electrode configuration;

FIG. 4B is a schematic representation of the heart of FIG. 4A employing a unipolar electrode configuration;

FIG. 5A is a schematic representation of a heart employing a bipolar electrode configuration;

FIG. 5B is a schematic representation of the heart of FIG. 5A employing a unipolar electrode configuration;

DETAILED DESCRIPTION OF THE PREFERRED EMBODIMENTS

Figure 1:
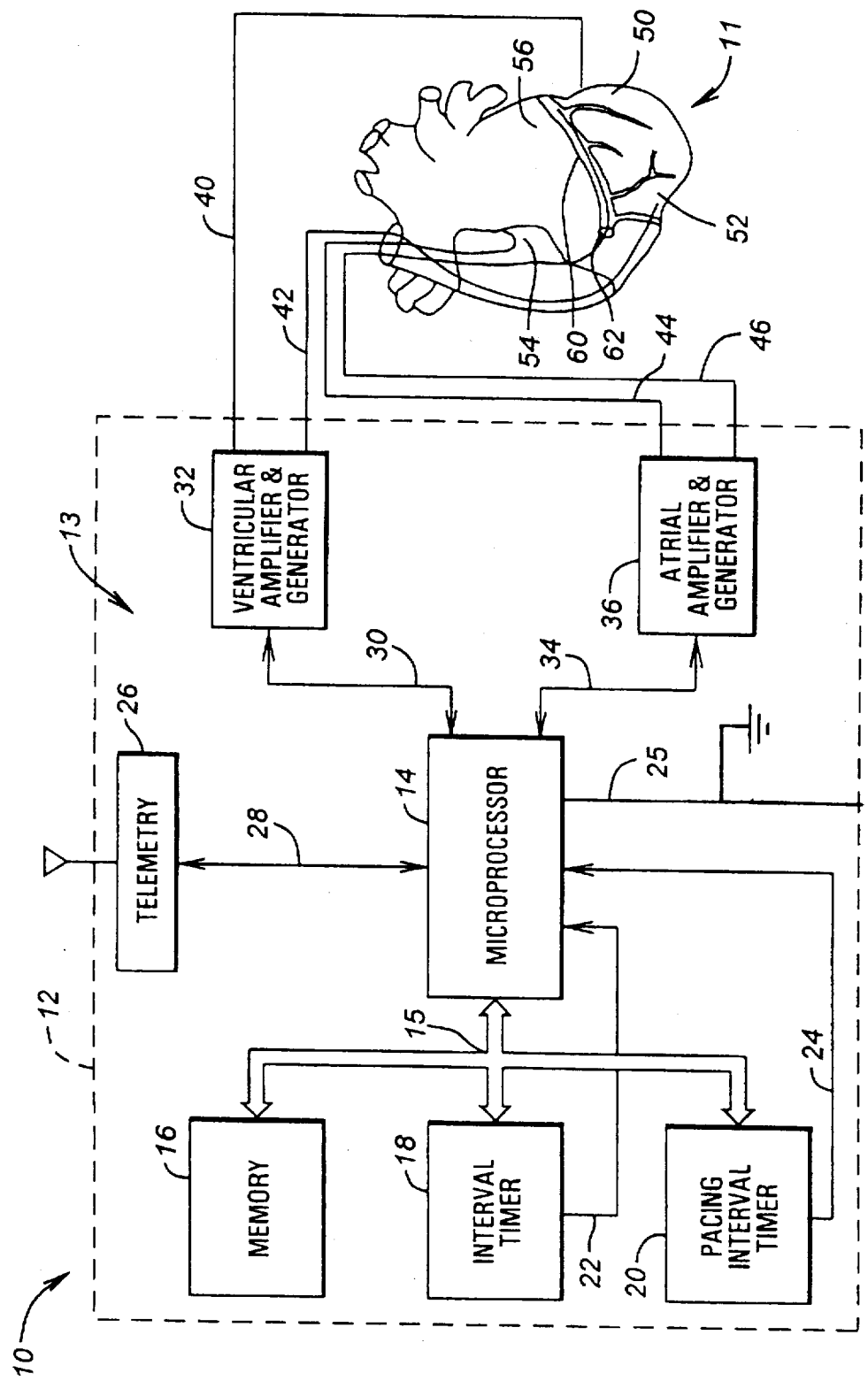
FIG. 1 is a block diagram of an implantable cardiac stimulator connected to a heart in a multiple-chamber electrode arrangement.

FIG. 1 is a block diagram illustrating an implantable cardiac stimulator 10 connected to a heart 11 in a multiple-chamber electrode arrangement. Stimulator 10 may be a pacemaker or other implantable pulse generator and comprises an outer conductive housing 12 having control circuitry 13 enclosed therein, Control circuitry 13 includes a microprocessor 14 which provides control and computational facilities for stimulator 10. Microprocessor 14 has input/output ports connected in a conventional manner via bi-directional bus 15 to memory 16, an interval timer 18, and a pacing interval timer 20. Interval timer 18 and pacing interval timer 20 have an output connected individually via lines 22 and 24, respectively, to a corresponding input port of microprocessor 14. Additionally, an indifferent or ground electrode 25 is referenced outside heart 11 and may be provided, for example, from housing 12 of stimulator 10. Electrode 25 is electrically connected to microprocessor 14.

Interval timers 18 and 20 may be external to microprocessor 14, as illustrated, or internal thereto. Additionally, these timers may be conventional up/down counters of the type that are initially loaded with a count value and count up to or down from the count value and output a roll-over bit upon completing the programmed count. The initial count value is loaded into interval timers 18 and 20 on bus 15. Respective roll-over bits are output to microprocessor 14 on lines 22 and 24. Memory 16 preferably includes both ROM and RAM. Generally, ROM stores operating routines, and RAM stores programmable parameters and variables.

Microprocessor 14 preferably also has an input/output port connected to a telemetry interface 26 via line 28. Stimulator 10, when implanted, is thus able to receive variable and control parameters from an external programmer and to send data to an external receiver if desired. As such, operating parameters stored within microprocessor 14 may be selectively altered non-invasively. Various suitable telemetry systems are known to those skilled in the art.

Microprocessor input/output ports connect via control line 30 to a ventricular sense amplifier and a ventricular pulse generator, shown at block 32 as a ventricular amplifier and generator. Microprocessor input/output ports also connect via control line 34 to an atrial sense amplifier and an atrial pulse generator, shown at block 36 as an atrial amplifier and generator. The atrial sense amplifier detects the occurrences of P-waves, and the ventricular sense amplifier detects the occurrences of R-waves. In addition, pulse parameter data, such as amplitude, width, enable/disable, and pulse initiation codes transmit to the atrial and ventricular pulse generators.

Stimulator 10 is connectable to have a multiple-chamber electrode arrangement. FIG. 1 shows a four chamber electrode arrangement connected to heart 11 of a patient. Ventricular amplifier and generator 32 is electrically connectable to two leads 40 and 42, and atrial amplifier and generator 36 is electrically connectable to two leads 44 and 46.

Lead 40 is an epicardial or endocardial type lead and connects to heart 11 at the left ventricle 50. Lead 42 is an endocardial type lead and connects to heart 11 in the right ventricle 52. In addition, lead 44 is a J-type lead extending to the right atrium 54, and lead 46 extends to the left atrium 56. Lead 46, for example, may be inserted into heart 11 through right atrium 54 and into the coronary sinus 60 by way of the coronary sinus ostium 62 in order to be positioned to stimulate the left atrium 56.

FIG. 1 shows a multiple-chamber electrode arrangement in which leads 42 and 44 are each positioned within a single chamber of the heart, and leads 40 and 46 are each positioned adjacent a single chamber. Those skilled in the art will recognize that these leads may be in various positions within, about, or adjacent chambers of the heart in order to establish a location for sensing and pacing. Further, various methods of lead implantation and fixation also are known.

Additionally, the present invention may be used with various implantable devices, with stimulator 10 in FIG. 1 illustrating an example of one such device. Stimulator 10, for example, may be a multiprogrammable, bipolar cardiac pulse generator designed to detect and terminate tachycardias and provide bradycardia pacing, such as the "INTERTACH II" or the "MARATHON II" each manufactured by Intermedics Inc. Other possible implantable devices may be directed solely or jointly to tachycardias, bradycardias, defibrillation, or pulse generation.

The overall operating method and algorithm of the present invention is more fully illustrated in a discussion of the flow diagrams and figures which follow. The flow diagrams represent the preferred embodiment of the program structure under which the microprocessor operates. The program structure may be written, for example, in a low level computer language and retained in a memory within the microprocessor.

Figure 2:
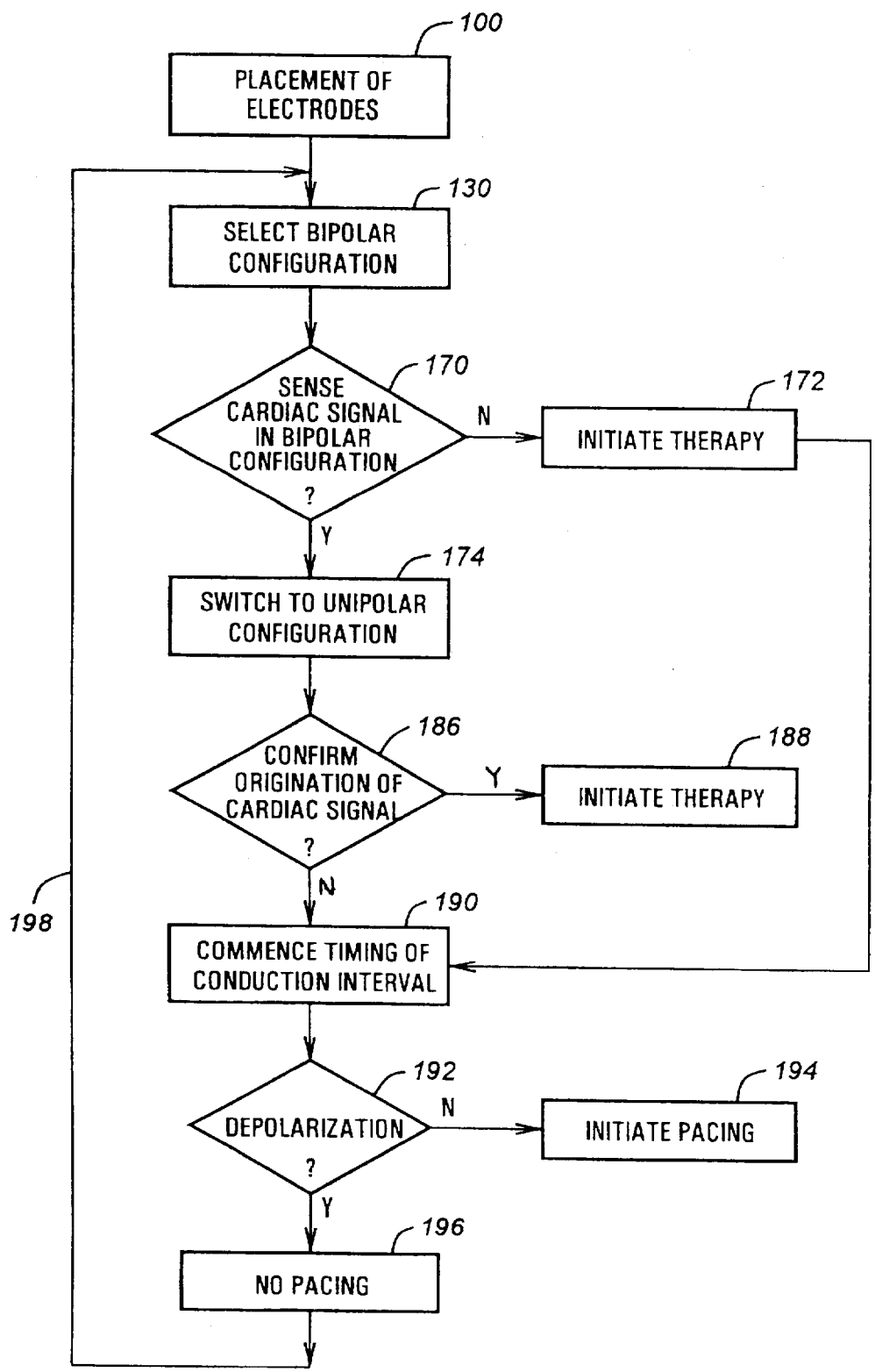
FIG. 2 is a flow diagram of the method and program structure according to the present invention.

Looking first to FIG. 2, a flow diagram shows an overview of the method and algorithm of the present invention. As shown in block 100, electrodes are placed for selected pacing and sensing of the heart. The electrodes may be placed in various dual or multiple-chamber arrangements or configurations depending upon the desired pacing and sensing capabilities needed. Possible multiple-chamber configurations include electrodes positioned in or adjacent to or electrically connected with two, three, or four chambers of the heart.

Figure 3A:
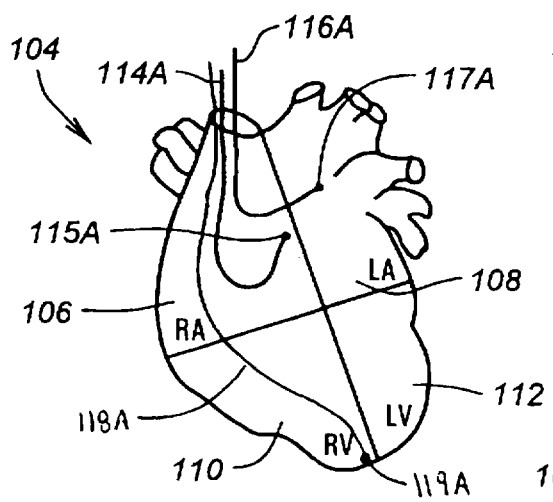
FIG. 3A is a schematic representation of a heart employing a first multiple-chamber electrode arrangement.
Figure 3B:
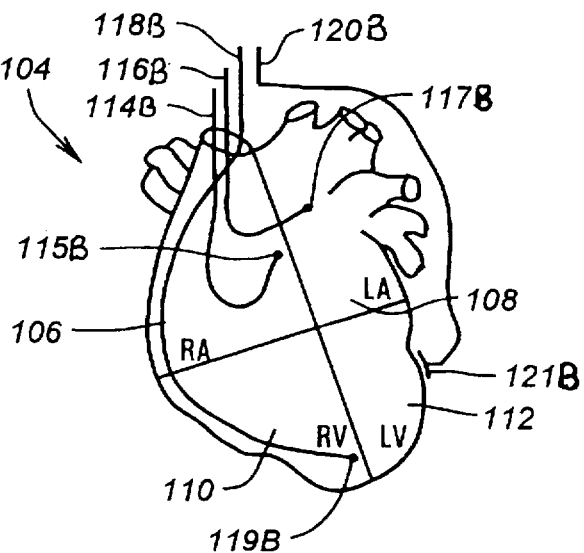
FIG. 3B is a schematic representation of a heart employing a second multiple-chamber electrode arrangement.

By way of example, FIGS. 3A and 3B illustrate two different multiple-chamber arrangements. Each of the figures depicts a schematic representation of a heart 104 having a right atrium 106, a left atrium 108, a right ventricle 110, and a left ventricle 112. FIG. 3A has a lead 114A with an electrode 115A positioned in right atrium 106, a lead 116A with an electrode 117A positioned adjacent left atrium 108, and a lead 118A with an electrode 119A positioned in right ventricle 110. FIG. 3B shows a lead 114B with electrode 115B in right atrium 106, a lead 116B with electrode 117B adjacent left atrium 108, a lead 118B with electrode 119B in right ventricle 110, and a lead 120B with electrode 121B adjacent left ventricle 112.

Each of the electrodes in FIGS. 3A and 3B may be positioned in, adjacent to, or electrically connected with a chamber or a selected area of the heart in order to effect sensing or pacing. In addition, the leads may have various configurations such as endocardial, epicardial, or the like, and may have a single electrode, such as a unipolar lead, or have two electrodes, such as a bipolar lead, or have numerous electrodes. Further, the electrodes may have various polarity configurations to pace and/or sense in one or more chambers of the heart.

Turning back momentarily to FIG. 2, after the leads and corresponding electrodes are placed in the heart per block 100, block 130 shows selection of a bipolar configuration.

FIGS. 4A, 4B, 5A, and 5B illustrate examples of this configuration. Each of these figures depicts a heart 104 having a right atrium 106, a left atrium 108, a right ventricle 110, and a left ventricle 112. Further, an implantable cardiac stimulator is represented at 132 and may be, for example, similar to stimulator 10 described in connection with FIG. 1. Stimulator 132 is generally shown as having a conductive housing 134 and two leads 136 extending from a header portion 138. Leads 136 may be bifurcated Y-connector leads to accommodate multiple-chamber configurations.

Looking now to FIG. 4A, a bipolar lead 140 is in right atrium 106, and a second bipolar lead 142 is adjacent left atrium 108. Lead 140 has a tip electrode 144 and a ring electrode 145, and lead 142 has a tip electrode 146 and a ring electrode 147. Leads 140 and 142 are shown in a bipolar configuration since sensing occurs between the two leads. Lines 148 represent the electromagnetic field lines between electrodes 144 and 146 in order to illustrate the bipolar configuration Looking to FIG. 5A, a bipolar lead 150 is in right atrium 106; a second bipolar lead 152 is in right ventricle 110; and a third lead 153 is in left ventricle 112. Lead 150 has a tip electrode 154 and a ring electrode 155; lead 152 has a tip electrode 156 and a ring electrode 157; and lead 153 has a tip electrode 159. Leads 152 and 153 are shown in a bipolar configuration since sensing occurs between the two leads. Lines 158 represent the electromagnetic field lines between the electrodes 156 and 159 in order to illustrate this bipolar configuration. It will be appreciated that all leads in the figures may have various configurations such as bipolar, unipolar, or other multiple electrode type leads known to those skilled in the art.

Turning back again to FIG. 2, after selection is made to the bipolar configuration, block 170 queries whether a cardiac signal is being sensed. If the answer to this query is negative and no signal is sensed, then the flow diagram proceeds to block 172 to initiate a therapy, such as pacing. If, on the other hand, the answer to this query is affirmative and a signal is sensed, then block 174 shows a switch to a unipolar configuration. FIGS. 4B and 5B illustrate an electrode arrangement which has been switched to a unipolar configuration.

Once in the unipolar configuration, sensing and/or pacing occurs between an electrode positioned to sense and/or pace the heart and a ground or indifferent electrode. In FIG. 4B, sensing and/or pacing occurs between tip electrode 146 of lead 142 and conductive housing 134 which acts as a ground electrode. An arrow 180 represents the occurrence of this sensing and/or pacing. Sensing and/or pacing also could occur between tip electrode 144 of lead 140 and conductive housing 134. In FIG. 5B, sensing and/or pacing occurs between tip electrode 156 of lead 152 and conductive housing 134. An arrow 182 represents the occurrence of this sensing and/or pacing. Sensing and/or pacing could also occur between tip electrode 159 of lead 153 and conductive housing 134.

Turning back to FIG. 2, once a switch is made to the unipolar configuration, block 186 queries the confirmation of the origin of the cardiac signal. If confirmation is made, then, as shown in block 188, therapy is initiated. If confirmation is not made, then, as shown at block 190, the program structure commences timing of a conduction interval. Reference is made to all of the FIGS. 3, 4, and 5 to illustrate the operation of blocks 186, 188, and 190.

In FIG. 4A, for example, as soon as a cardiac signal is initially detected in the bipolar configuration, the origination of that signal may not be known. For example, lead 142 in left atrium 108 may detect a cardiac signal. This signal, however, may have originated in the SA node in right atrium 106. Alternatively, this signal may have originated elsewhere, for instance as an ectopic signal in left atrium 108. Similarly, in FIG. 3B, as soon as a cardiac signal is detected in the bipolar mode, the originating location of that signal may not be known. For instance, lead 118B in FIG. 3B may detect a signal which commenced as an ectopic beat in left ventricle 112 and propagated to right ventricle 110. Alternatively, the signal may have originated from right ventricle 110 and propagated to the SA node.

In order to confirm where the cardiac signal originated, the electrode arrangement is immediately switched from the bipolar configuration to the unipolar configuration. Switching from the bipolar to the unipolar configuration verifies the origination of the signal. Looking to FIG. 4A, if, for example, a cardiac signal originated in left atrium 108 as an arrhythmia, this signal would be detected in the bipolar configuration. A switch then would occur to the unipolar configuration. Once in the unipolar configuration, lead 142 in left atrium 108 would immediately detect the presence of the signal. The immediate detection of this signal confirms after discrimination from the ventricle the signal originated in the left atrium. In turn, as shown in block 188, the stimulator would initiate a therapy, such as pacing. Suppose instead, an intrinsic cardiac signal originated in right atrium 106 at the SA node. This signal would be detected in the bipolar configuration, and a switch would occur to the unipolar configuration. Once in the unipolar configuration, lead 142 in left atrium 108, however, would not immediately detect the presence of the signal since a definitive amount of time is required for the signal to propagate to left atrium 108. This delay in time would confirm the signal originated in right atrium 106.

Turning back again to FIG.2, once a switch is made to the unipolar configuration, the stimulator commences to time a conduction interval, as shown in block 190. Next, block 192 queries whether depolarization or propagation has occurred. If the answer to this query is negative, pacing is initiated, as shown in block 194. If the answer to this query is positive, no pacing is initiated, as shown in block 196. The program structure then loops back along line 198 to block 130. Reference is made to all of the FIGS. 3, 4, and 5 for illustration purposes.

In FIGS. 4A and 4B, for example, if the answer to block 186 is negative and a signal originates in right atrium 106, then the stimulator commences to time a conduction interval, as shown in block 190. In FIGS. 4A and 4B, this interval is equal to an intra-atrial conduction time (i.e., the time required for a P-wave cardiac signal to propagate from right atrium 106 to left atrium 108). If the cardiac signal properly propagates and is detected in left atrium 108 before the end of the intra-atrial conduction time, then no pacing or therapy is initiated, as shown in block 196. If, however, proper propagation does not occur and no cardiac signal is detected in left atrium 108, then pacing is initiated, as shown in block 194.

FIGS. 5A and 5B illustrate yet another example. If the answer to block 186 is negative and a signal originates in right atrium 106, then the stimulator commences to time a conduction interval as shown in block 190. In FIG. 5A, this interval is a ventricular conduction time (i.e., the time required for an intrinsic cardiac conduction signal to properly propagate from the SA node to right ventricle 110). If the cardiac signal properly propagates and is detected in right ventricle 110 before the end of the conduction time, then no pacing or therapy is initiated. If, however, proper propagation does not occur and no cardiac signal is detected in right ventricle 110, then pacing is initiated.

FIG. 3B illustrates another example. If the answer to block 186 is negative and a signal originates in right atrium 106, then the stimulator commences to time a conduction interval as shown in block 190. If the cardiac signal properly propagates and is detected in left ventricle 112 before the end of the conduction time, then no pacing therapy is initiated, as shown in block 196. If, however, proper propagation does not occur and no cardiac signal is detected in left ventricle 112, then pacing is initiated, as shown in block 194.

As one advantage, the present invention may be utilized to treat cardiac disorders. For example, the left atrium of the heart may be stimulated after the intra-atrial conduction time elapses to assure that the left atrium contracts before the left ventricle. Stimulation of the left atrium before the left ventricle aids to prevent DDD syndrome. Additionally, the left atrium may be pre-stimulated before stimulation of the right atrium. Stimulation of the left atrium before the right atrium aids to reduce the occurrence of a potential atrial arrhythmia.

Figure 6A:
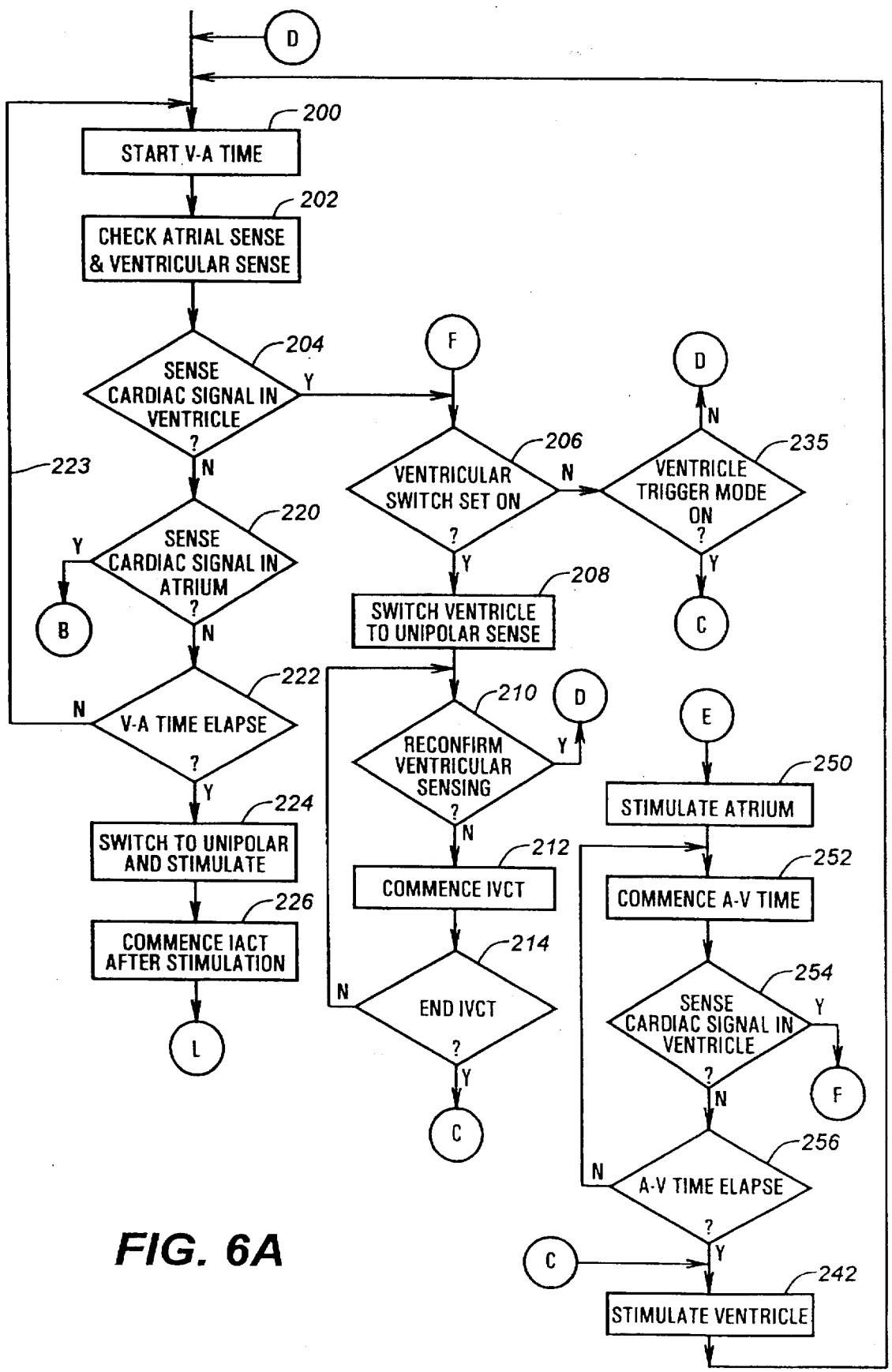
FIG. 6A is a detailed flow diagram of the program structure according to the present invention.
Figure 6B:
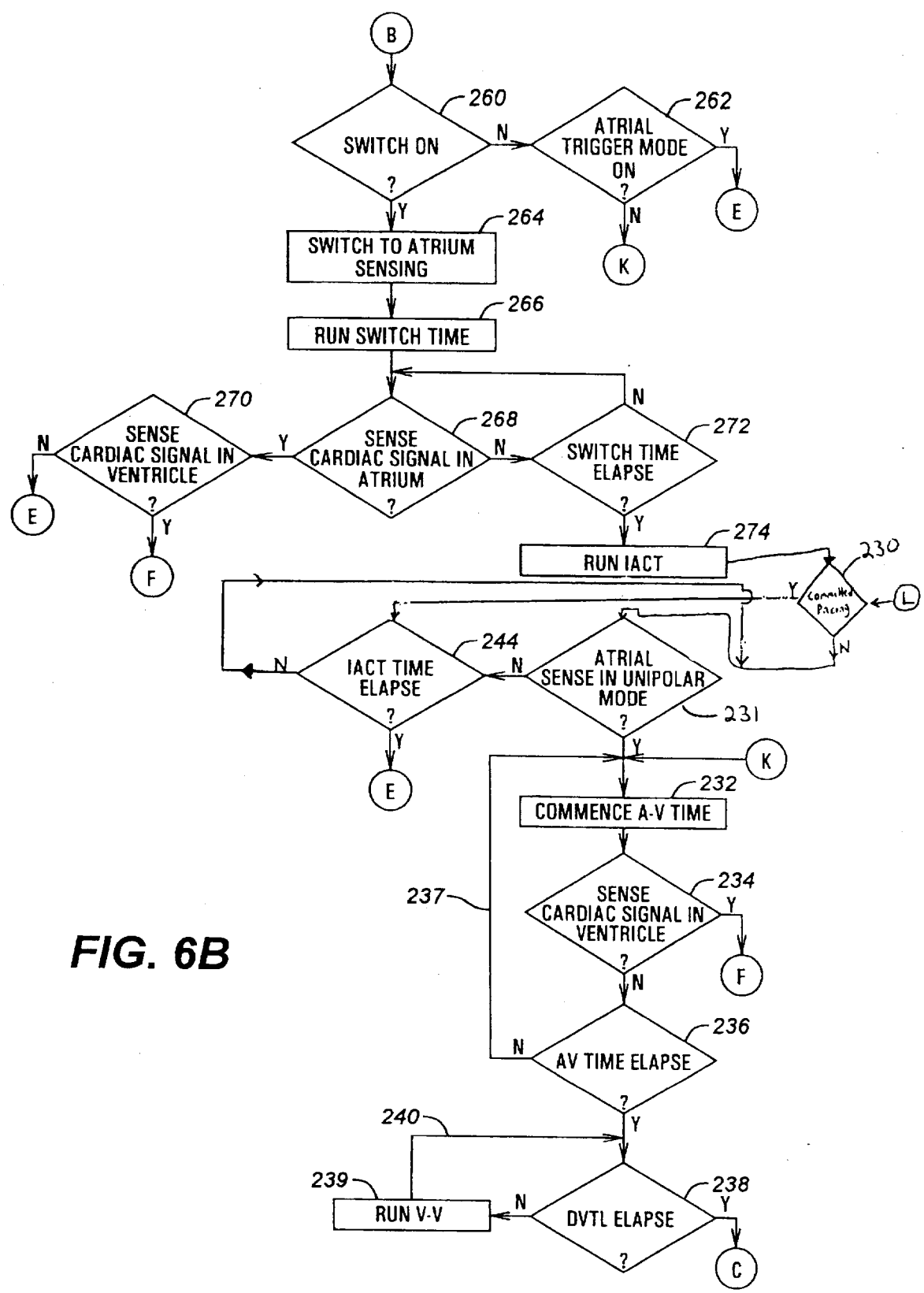
FIG. 6B is a continuation of the detailed flow diagram of FIG. 6A.

FIGS. 6A and 6B illustrate a detailed flow diagram of the program structure of the present invention. The program structure commences at block 200 with start ventricular-atrial (V-A) time. During the V-A time, block 202 shows a check for atrial sense and a check for ventricular sense. The atrial sensing is done in a bipolar configuration, and the ventricular sensing is done in either a bipolar or unipolar configuration. Next, block 204 queries whether a cardiac signal is sensed in the ventricle. If the answer to this query is affirmative, the cardiac signal sensed in the ventricle is considered an extraneous or ectopic beat, and the program structure proceeds to section F.

At section F, block 206 queries whether the ventricular switch is set on. If the answer to this query is affirmative, then the ventricle is switched to unipolar sense as shown in block 208. Next block 210 queries whether the ventricle is reconfirming sensing in the unipolar configuration. If the answer to this query is affirmative, then the program structure proceeds to section D and to block 200. If the answer to this query is negative, then, as at block 212, an intra-ventricular conduction time (IVCT) commences. Block 214 then queries whether the IVCT has ended. If the answer to this query is negative, then the program structure loops back along line 215 to block 210. If, on the other hand, the answer is affirmative, the program structure proceeds to section C.

Turning back now to block 204, if the answer to the query is negative, then the program structure proceeds to block 220. This block queries whether a cardiac signal is sensed in the atrium. If the answer to this query is positive, then the program structure proceeds to section B. If the answer is negative, then block 222 queries whether the V-A time has elapsed. If the answer to this query is negative, then the program structure loops back along line 223 to block 200. If the answer to the query is affirmative, then a switch is made to the unipolar configuration and then stimulation is initiated, as shown in block 224. After stimulation occurs in block 224, block 226 shows commencing the intra-atrial conduction time (IACT). After block 226, the program structure continues to section L.

At section L, block 230 queries whether a commitment to pacing exists. If the answer is negative, then block 231 queries whether a cardiac signal is sensed in the atrium while in the unipolar configuration. If the answer is affirmative, then block 232 shows to commence the AN time. Next, block 234 queries whether a cardiac signal is sensed in the ventricle while in either an unipolar or bipolar configuration. If the answer to this query is affirmative, then the program structure proceeds to section F. As noted at section F, block 206 queries whether the ventricular switch is on. If the answer is negative, the program structure proceeds to block 235. Block 235 queries whether the ventricular trigger mode is on. If the answer to this query is positive, the program structure proceeds to section C. If the answer is negative, the program structure proceeds to section D.

If the answer to block 234 is negative, block 236 queries whether the AV time has elapsed. If the time has not elapsed, then the program structure loops back along line 237 to block 232. If the time has elapsed, then block 238 queries whether the dynamic ventricular tracking limit (DVTL) time has elapsed; for further discussion on DVTL, see U.S. Pat. application Ser. No. 08/433,788 entitled "Improved Control of Pacing Rate in Dual-Chamber, Rate Adaptive Pacemakers now U.S. Pat. No. 5,609,613." If the answer to this query is negative, then the program structure proceeds to block 239 and then loops back along line 240 to block 238. Block 239 holds pacing for a pre-determined time of V—V. If the answer to block 238 is positive, then the program structure proceeds to section C. At section C, block 242 shows stimulation of the ventricle in either the unipolar or bipolar configuration.

Looking back now to block 230, if the answer to this query is affirmative, then block 244 queries whether the IACT has elapsed. If the answer to this query is negative, then the program structure proceeds to block 231. If the answer is affirmative, then the program structure proceeds to section E.

At section E, block 250 shows stimulation of the atrium in the bipolar configuration. Next the program structure commences the A-V time, as shown in block 252. Block 254 then queries whether a cardiac signal is sensed in the ventricle while in the bipolar or unipolar configuration. If the answer to this query is affirmative and a ventricular event is sensed, then the program structure proceeds to section F. If the answer is negative, block 256 queries whether the A-V time has elapsed. If the time has not elapsed, then the program structure loops back along to line 258 to block 252. If the time has elapsed, the program structure proceeds to block 242 which shows stimulation of the ventricle.

Turning back to block 220, if the answer to this query is affirmative, then the program structure proceeds to section B. At section B, block 260 queries whether the switch is on. If the answer is negative, then the program structure proceeds to block 262. Block 262 queries whether the atrial trigger mode is on. If the answer is affirmative, then the program structure proceeds to section E and block 250. If the answer is negative, then the program structure proceeds to section K and block 232.

Looking back to the query of block 260, if the answer is affirmative, then a switch is made to atrial sensing in the unipolar configuration, as shown at block 264. Then, at block 266, the program structure runs switch time. Block 268 then queries whether a cardiac signal is sensed in the atrium while in unipolar configuration. If the answer is affirmative, then block 270 queries whether a cardiac signal is sensed in the ventricle. If a signal in the ventricle is sensed, the program structure proceeds to section F and block 206. If no signal is sensed, the program structure proceeds to section E and block 250.

Turning back to the query of block 268, if the answer is negative and no cardiac signal is sensed in the atrium, then block 272 queries whether the switch time has elapsed. If this time has not elapsed, then the program structure proceeds to block 268. If this time has elapsed, block 274 commences to run the IACT with either the left atrium or the right atrium.

Since certain changes may be made in the above-described apparatus and method without departing from the scope of the invention herein involved, all matter contained in the description or shown in the accompanying drawings shall be interpreted as illustrative and not in a limiting sense.

I claim:

1. A method for determining the origin of a cardiac signal in a heart, comprising the steps of:
   providing first and second electrodes connected to said heart, and a third electrode referenced outside said heart;
   providing said first electrode for sensing a first chamber of said heart;
   providing said second electrode for sensing a second chamber of said heart;
   sensing for said cardiac signal while said first and second electrodes are in a bipolar configuration;
   detecting said cardiac signal with said first and second electrodes;
   switching both said first and second electrodes to a unipolar configuration after detecting said cardiac signal; and
   sensing for said cardiac signal between said first and second electrodes and said third electrode in said unipolar configuration; and
   determining the origin of said cardiac signal in one of said first and second chambers.

2. The method of claim 1 further comprising the steps of:
   positioning said second electrode to sense a signal from a left atrium of said heart;
   providing said third electrode as a ground electrode;
   sensing for said cardiac signal in said unipolar configuration between said second electrode and said third electrode.

3. The method of claim 1 further comprising the step of pacing said first chamber if said cardiac signal originates in said second chamber.

4. The method of claim 1 further comprising the steps of:
   providing said first electrode for one of sensing and pacing a first chamber of said heart;
   providing said second electrode for one of sensing and pacing a second chamber of said heart;
   commencing a conduction time interval if said cardiac signal originates in said first chamber;
   sensing for said cardiac signal in said second chamber between said second electrode and said third electrode while in said unipolar configuration; and
   pacing said second chamber if after said conduction time interval elapses said cardiac signal is not sensed in said second chamber.

5. The method of claim 4 in which:
   said first chamber is a right atrium of said heart;
   said second chamber is a left atrium of said heart; and
   said conduction time interval is equal to an intra-atrial conduction time.

6. The method of claim 4 in which:
   said first chamber is a right ventricle of said heart;
   said second chamber is a left ventricle of said heart; and
   said conduction time interval is equal to an intra-ventricular conduction time.

7. A method for verifying propagation of a cardiac signal in a heart, comprising the steps of:
   providing a first electrode electrically connected with a first atrial chamber of said heart;
   providing a second electrode electrically connected with a second atrial chamber of said heart;
   providing a ground electrode outside said heart;
   providing said first and second electrodes in a bipolar configuration in which one of pacing and sensing occur between said first and second electrodes;
   pacing said first chamber to induce a cardiac signal;
   commencing a conduction time interval;
   switching both said first and second electrodes to a unipolar configuration in which sensing occurs between said second electrode and said ground electrode;
   sensing for said cardiac signal in said second chamber with said ground and second electrodes in said unipolar configuration; and
   verifying propagation of said signal if said cardiac signal is sensed in said second chamber.

8. The method of claim 7 further comprising the step of pacing said second chamber if after said conduction time interval elapses said cardiac signal is not sensed in said second chamber.

9. The method of claim 7 further comprising the step of switching said first and second electrodes back to said bipolar configuration after sensing for said cardiac signal in said unipolar configuration.

10. The method of claim 9 in which:
    said conduction time interval is about equal to a time required for said cardiac signal to propagate from said first chamber to said second chamber; and
    said switching occurs after said conduction time interval elapses.

11. An implantable medical device for determining the origin of a cardiac signal in a heart, comprising:
    a conductive housing;
    control circuitry enclosed within said housing;
    a first electrode electrically connected to said control circuitry, and electrically connectable with a first chamber of said heart;
    a second electrode electrically connected to said control circuitry, and electrically connectable with a second chamber of said heart;
    an indifferent electrode electrically connected to said housing;
    means for connecting said first and second electrodes in a bipolar configuration, wherein sensing for said cardiac signal occurs between said first and second electrodes;
    means for switching said first and second electrodes to a unipolar configuration after said cardiac signal is sensed in said bipolar configuration, wherein sensing for said cardiac signal occurs between said indifferent and second electrodes: and
    means responsive to a detected signal at one said first or second electrodes in unipolar configuration for determining the origin of said signal in said first or second chamber of said heart.

12. The implantable medical device of claim 11 further comprising means for pacing said first chamber if said cardiac signal originates in said second chamber.

13. The implantable medical device of claim 11 in which:
said first chamber is the right atrium of said heart; and
said second chamber is the left atrium of said heart.

14. The implantable medical device of claim 13 further comprising means for stimulating said left atrium after an intra-atrial conduction time so said left atrium contracts before the left ventricle of said heart.

15. The implantable medical device of claim 13 further comprising
means for stimulating said right atrium,
means for stimulating said left atrium; and
means for controlling said stimulating means to stimulate said left atrium before said right atrium in order to reduce occurrence of an atrial arrhythmia in said left and right atria.

16. The implantable medical device of claim 11 in which:
said first chamber is a right ventricle of said heart; and
said second chamber is a left ventricle of said heart.

* * * * *